(12) United States Patent
Jarofski

(10) Patent No.: US 10,365,241 B2
(45) Date of Patent: Jul. 30, 2019

(54) SENSING SYSTEM FOR A HUMIDITY SENSOR

(71) Applicant: Veris Industries, LLC, Tualatin, OR (US)

(72) Inventor: Dieter Jarofski, Tualatin, OR (US)

(73) Assignee: Veris Industries, LLC, Tualatin, OR (US)

(*) Notice: Subject to any disclaimer, the term of this patent is extended or adjusted under 35 U.S.C. 154(b) by 86 days.

(21) Appl. No.: 15/097,809

(22) Filed: Apr. 13, 2016

(65) Prior Publication Data

US 2016/0334354 A1    Nov. 17, 2016

Related U.S. Application Data

(60) Provisional application No. 62/160,979, filed on May 13, 2015.

(51) Int. Cl.
G01N 27/22    (2006.01)

(52) U.S. Cl.
CPC ......... *G01N 27/225* (2013.01); *G01N 27/223* (2013.01)

(58) Field of Classification Search
CPC ........................... G01N 27/225; G01N 27/223
See application file for complete search history.

(56) References Cited

U.S. PATENT DOCUMENTS

| 5,414,400 | A | 5/1995 | Gris et al. |
| 6,313,623 | B1 | 11/2001 | Kojovic et al. |
| 7,227,441 | B2 | 6/2007 | Skendzic et al. |
| 7,227,442 | B2 | 6/2007 | Skendzic |
| 7,538,541 | B2 | 5/2009 | Kojovic |
| 7,564,233 | B2 | 7/2009 | Kojovic |
| 7,902,812 | B2 | 3/2011 | Kojovic |
| 7,986,968 | B2 | 7/2011 | Dobrowski et al. |
| 8,330,449 | B2 | 12/2012 | Greenberg |
| 8,872,611 | B2 | 10/2014 | Rouaud et al. |
| 9,442,139 | B2 | 9/2016 | Hobelsberger et al. |
| 9,448,258 | B2 | 9/2016 | Garabieta et al. |
| 2011/0005313 | A1* | 1/2011 | Vernon ............... G01N 27/225 73/335.04 |
| 2011/0043190 | A1 | 2/2011 | Farr |
| 2013/0139587 | A1* | 6/2013 | Le Neel ............... G01N 27/223 73/335.04 |
| 2014/0216153 | A1* | 8/2014 | Pion ..................... G01N 27/225 73/335.04 |
| 2016/0055963 | A1 | 2/2016 | Lockstedt et al. |
| 2016/0091535 | A1 | 3/2016 | Bannister et al. |

FOREIGN PATENT DOCUMENTS

| WO | 2006108021 A2 | 10/2006 |
| WO | 2012022779 A1 | 2/2012 |

* cited by examiner

*Primary Examiner* — Xin Y Zhong
(74) *Attorney, Agent, or Firm* — Chernoff, Vilhauer, McClung & Stenzel, LLP

(57) ABSTRACT

A humidity sensor that includes a humidity sensitive material. A sensing circuit associated with the humidity sensitive material estimates the ambient humidity based upon the humidity sensitive material. A heating element is associated with the humidity sensitive material. A temperature circuit increases the temperature proximate the humidity sensitive material and thereafter the sensing circuit estimates the ambient humidity.

18 Claims, 8 Drawing Sheets

SENSING SYSTEM FOR A HUMIDITY SENSOR

CROSS-REFERENCE TO RELATED APPLICATIONS

This application claims the benefit of U.S. Provisional Application No. 62/160,979, filed May 13, 2015.

BACKGROUND OF THE INVENTION

The present invention relates to a sensing system for a humidity sensor.

Humidity relates to the amount of water vapor that exists in the air. One measure of humidity is relative humidity which is the amount of water vapor in a sample of air compared to the maximum amount of water vapor the air can hold at any specific temperature. Relative humidity may be defined as the ratio of the partial pressure of water vapor in a gaseous mixture of air and water vapor to the saturated vapor pressure of water at a given temperature. Relative humidity may be expressed as a percentage in the following manner:

$$RH = \frac{p_{(H_2O)}}{p^*_{(H_2O)}} \times 100\%$$

where $p(H_2O)$ is the partial pressure of water vapor in the gas mixture; $p^*(H_2O)$ is the saturation vapor pressure of water at the temperature of the gas mixture; and RH is the relative humidity of the gas mixture being considered.

Another measure of humidity is absolute humidity which is the quantity of water in a particular volume of air. The amount of vapor in that volume of air is the absolute humidity of that volume of air. One equation representing absolute humidity (e.g., AH) is the mass of water vapor $m_w$, per cubic meter of air, $V_a$.

$$AH = \frac{m_w}{V_a}$$

Specific humidity is the ratio of water vapor to air (including water vapor and dry air) in a particular volume. Specific humidity ratio is expressed as a ratio of kilograms of water vapor, $m_w$, per kilogram of mixture, $m_t$.

The specific humidity (e.g., SH) ratio can be expressed as:

$$SH = \frac{m_w}{m_a + m_v}$$

Specific humidity is related to a mixing ratio (and vice versa) by:

$$SH = \frac{MR}{1 + MR}$$

$$MR = \frac{SH}{1 - SH}$$

Other measures of humidity may be used, typically depending on the particular application.

Humidity sensors tend to have limited accuracy in providing a repeatable measurement due to hysteresis within the sensor itself. A humidity sensor with hysteresis may be in any number of states, independent of the inputs to the humidity sensor. More precisely, the hysteresis of a humidity sensor exhibits path-dependence, or rate-independent memory. Accordingly, humidity sensors with hysteresis are problematic to predict the output without knowing the history of the input. Thus, in order to predict the output, the path that the input followed before it reached its present value needs to be known.

Some humidity sensors have limited hysteresis relative to sensor repeatability but tend to be relatively expensive. While generally accurate, such sensors tend to be to expensive for many applications. Other humidity sensors have significant hysteresis relative to sensor repeatability but tend to be relatively inexpensive. While sufficiently inexpensive, such sensors may be too inaccurate for many applications.

What is desired therefore, is a relatively inexpensive sensing system for a humidity sensor that has relatively low dependence on it hysteresis.

The foregoing and other objectives, features, and advantages of the invention will be more readily understood upon consideration of the following detailed description of the invention, taken in conjunction with the accompanying drawings.

DETAILED DESCRIPTION OF PREFERRED EMBODIMENT

Figure 1:
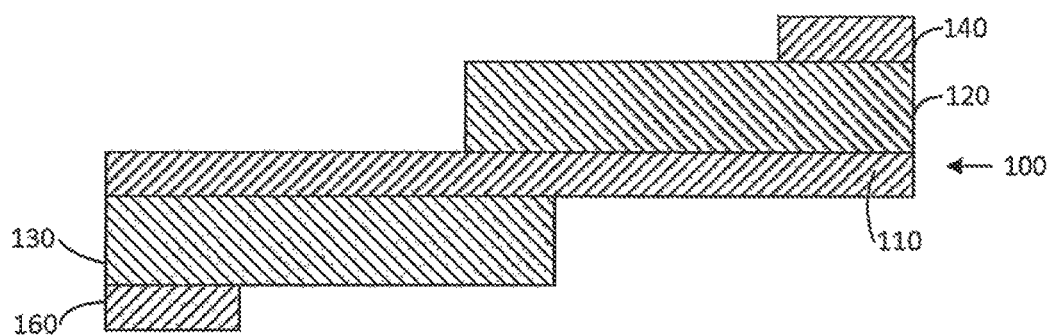
FIG. 1 illustrates an exemplary humidity sensor.

One example of a humidity sensor is a capacitance-based humidity sensor element in the form of a thin flexible film. Referring to FIG. 1, a capacitance-based humidity sensor 100 includes a dielectric film core 110 having a pair of electrically conductive layers 120, 130 on opposite sides thereof. Contacts 140, 160 on layers 120, 130 connect the sensor element to a source of electrical current.

The dielectric film 110 is a water absorbing material having a dielectric constant which changes predictably (preferably, essentially linearly) as a function of relative humidity. The dielectric film may have backbone chains containing heterocyclic units in which one or more atoms in the heterocyclic unit is nitrogen, one or more carbon atoms in the heterocyclic unit has an oxygen atom double bonded to it (i.e., the unit contains one or more keto groups), and the heterocyclic unit is bonded into the polymer backbone through one or more nitrogen atoms of the heterocyclic ring. The resulting change in capacitance for a given change in humidity is preferably constant over a temperature range of about 15° to 50° C., allowing the humidity sensor to be employed in harsh conditions.

The dielectric film may be made as thin as possible for the desired capacitance and film strength. The film is preferably thinner than the conductive layers. The film 110 may, for example, have a thickness of 0.005 inches or less. The resulting element 100 is relatively light and thin. The dielectric layer 110 may be made prior to the formation of the outer bonded conducting layers 120 and 130.

Figure 2:
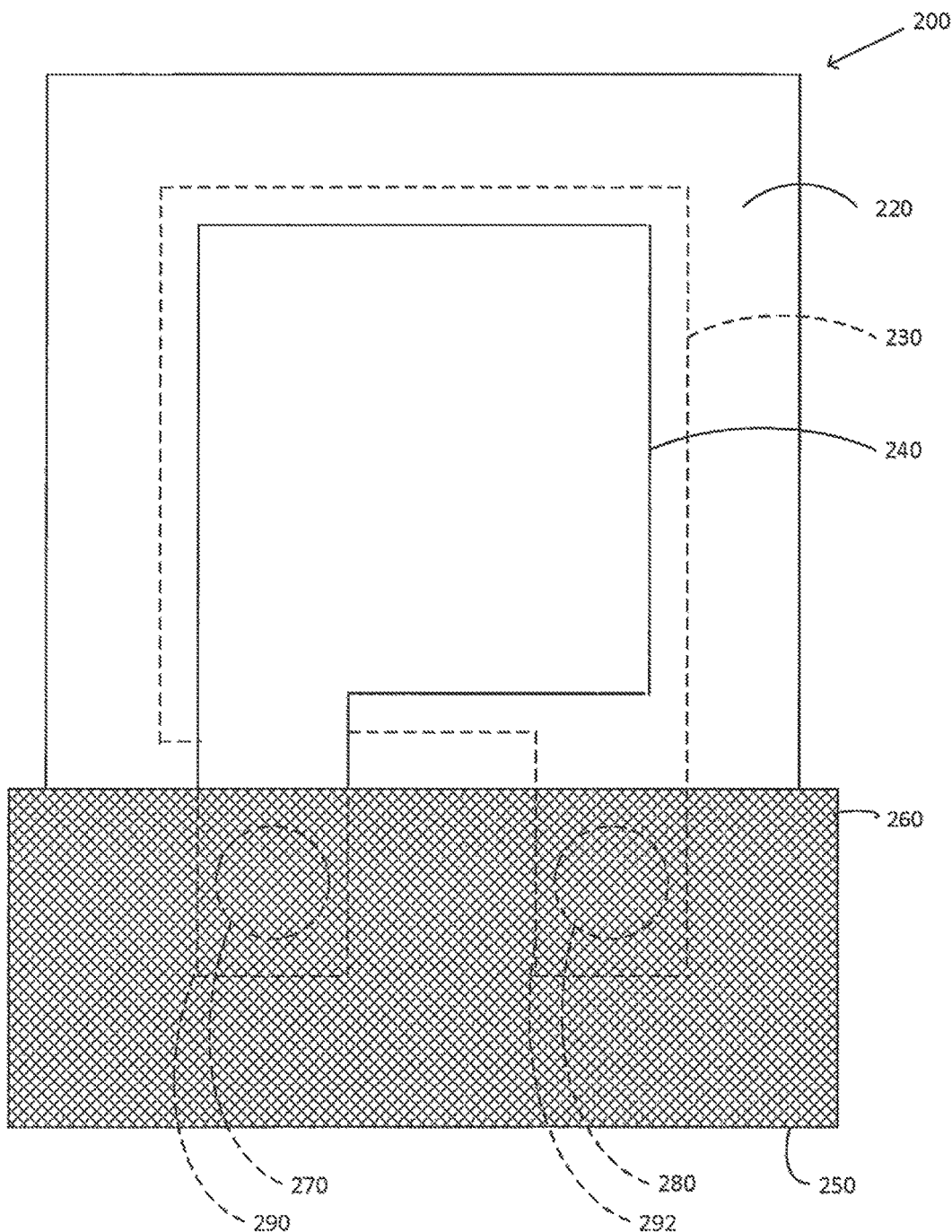
FIG. 2 illustrates another exemplary humidity sensor.

FIG. 2 illustrates a humidity sensor 200 that includes a dielectric film 220 with a pair of conductive layers 230, 240 formed on opposite sides of film 220, together with a holder 260. Outer conductive layers 230, 240 form the plates of the capacitor. Layers 230, 240 cover selected areas on opposite sides of dielectric film 220. The overlapping areas of the conductive layers 230, 240 comprise the active portion of the capacitance humidity sensor. Regions 270, 280 of conductive material are applied over the conducting layers 230, 240 in areas where the layers 230, 240 do not overlap, for example in elongated tab portions 290, 292, which extend into holder 260. Electrical contact is made to the regions 270, 280 by one or more conductive metal plates 250 forming part of holder 260 used to mount the humidity sensor. Many humidity sensors are provided in the form of an integrated circuit package together with associated electronics and sensing structures. The humidity sensor, may be for example, an active or a passive device. Alternatively, it is to be understood that any humidity sensor of any configuration and design may be used.

Figure 3:
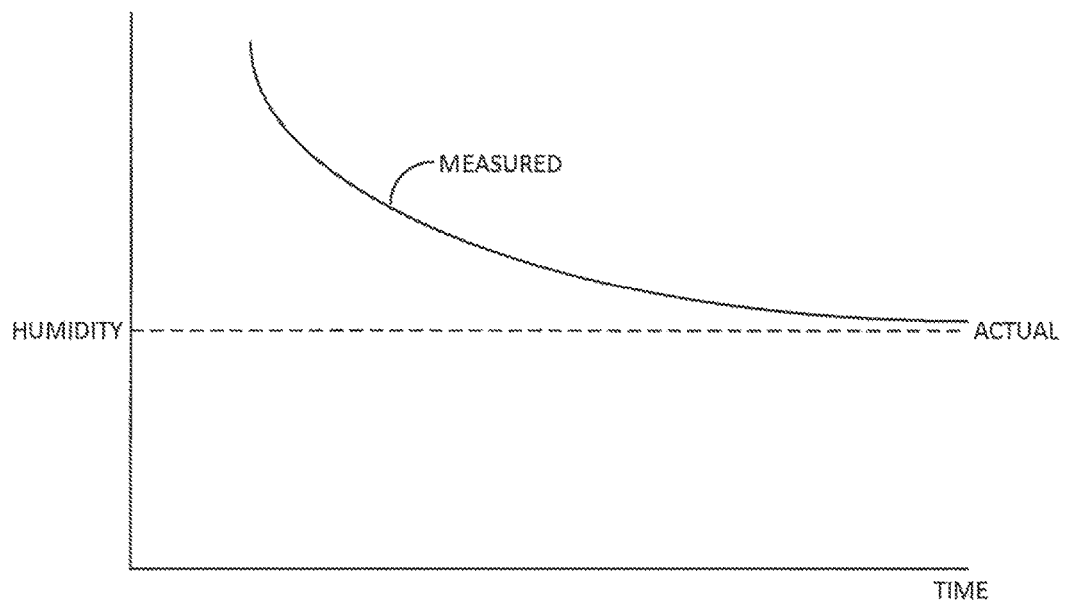
FIG. 3 illustrates an exemplary decrease in humidity.

Referring to FIG. 3, typically a humidity sensor has a characteristic that for a relatively quick change from an initial ambient humidity to a lower ambient humidity results in a decrease in the sensed humidity value over time. The characteristics of the curve depend on the previous state of the humidity sensor, the humidity levels, among a variety of other factors.

Figure 4:
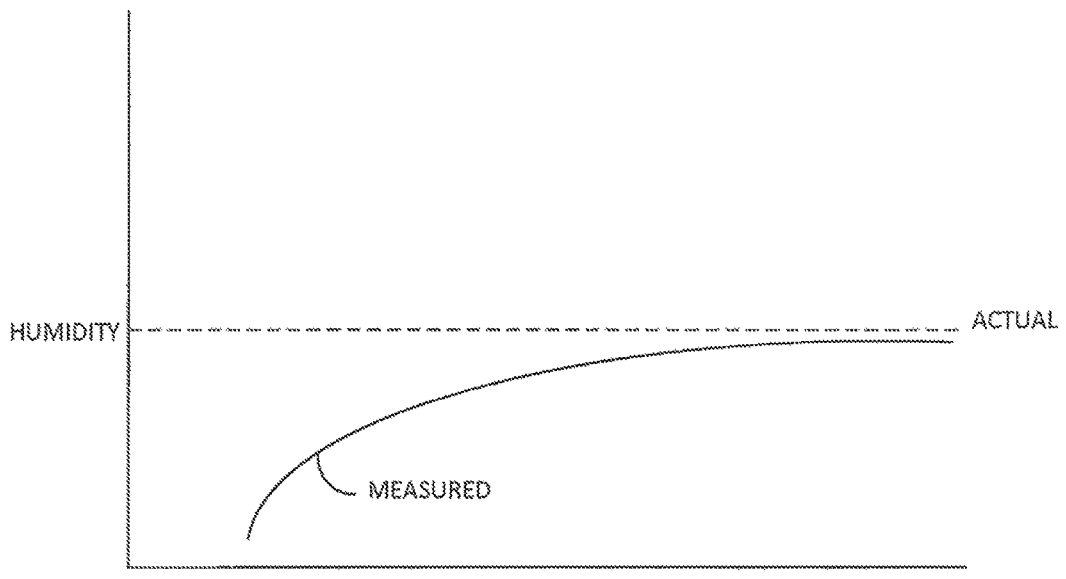
FIG. 4 illustrates an exemplary increase in humidity.

Referring to FIG. 4, typically a humidity sensor has a characteristic that for a relatively quick change from an initial ambient humidity to a higher humidity results in an increase in the sensed humidity value over time. The characteristics of the curve depend on the previous state of the humidity sensor, the humidity levels, among a variety of other factors.

Depending on the previous state of the humidity, an increase from a lower value to a higher value, or from a higher value to a lower value, the hysteresis typically results in an offset to the actual humidity value. In general, the offset of the hysteresis is generally unknown unless the system tracks the history of the changes in humidity. Moreover, the tracking of the humidity and the state of the humidity sensor is a complicated process, at best. As a result of the hysteresis, an error results in the measurement with the actual humidity being an unknown value. Moreover, since the history of the humidity sensor is unknown, simply calibrating the device is not suitable to remove a substantial part of the hysteresis.

In order to implement a relatively inexpensive humidity sensor that tends to have significant hysteresis, it was determined that it is desirable to change the environment proximate the sensor to achieve a known hysteresis state. By way of example, one known hysteresis state is to change the humidity sensor to a humidity state of zero which will have a corresponding hysteresis of zero. Since the ambient humidity tends to shift relatively slowly over time, it is desirable to use a heating device proximate the humidity sensor to temporarily decrease the sensed humidity to zero. Removing the moisture from the humidity sensor can be performed by heating the air proximate the sensor and/or the sensor itself which has the same and an accelerated effect. In this manner, the environment is changed to 0% humidity, and then subsequently re-exposed to ambient humidity conditions. By way of example, the heater provides the mechanism to cause the change. The heater does not necessarily need to be in direct contact with the sensing device (i.e. one embodiment may include heating the sensor through the back side of its supported printed circuit board). In this manner, heating the humidity sensor or the air proximate thereof tends to remove the moisture from the humidity sensor. Preferably the heater is incorporated on the same integrated package as the humidity sensor. By decreasing the sensed humidity of the humidity sensor, to a known value, such as zero percent humidity, the humidity sensor is brought to a known state. Thereafter, the humidity sensor is permitted to increase in humidity until the humidity sensor is sensing the ambient humidity. The ambient humidity may be determined by sensing the humidity when the temperature of the humidity sensor reaches the ambient temperature of the environment, such as for example, by the humidity sensor cooling off after being heated. The ambient temperature of the environment may be determined, for example, based upon a temperature sensor that is not as influenced by the temperature sensor associated with the humidity sensor. In this manner, humidity measurement will be based upon a known hysteresis curve. In this manner, the curve upon which the humidity measurement is obtained is generally known and may be effectively characterized. Also, the direction of the curve will be generally known because the sensor is decreased in its humidity until it reaches the known low level, such as zero, and the characteristics of the curve to reach the humidity of the current environment are likewise generally known. Alternatively, any other embodiment may be used that temporarily modifies the relatively humidity of the sensing environment to substantially 0% and then re-exposes the sensor to the ambient conditions.

By way of example, the known state of the humidity sensor may likewise be substantially zero, if desired. In addition, the known state of the humidity sensor may likewise be less than 10% of a full scale measurement, more preferably less than 5% of a full scale measurement, more preferably less than 3% of a full scale measurement, and more preferably less than 1% of a full scale measurement. For example, a full scale measurement may be from 0% to 100%, or from 5% to 90%. By way of example, the temperature of the humidity sensor and the temperature of the ambient environment at which the humidity measurement is made may be substantially the same, if desired. In addition, the temperature of the humidity sensor and the temperature of the ambient environment at which the humidity measurement is made may be less than 10% of a difference from one another, more preferably less than 5% of a difference from one another, more preferably less than 3% of a difference from one another, and more preferably less than 1% of a difference from one another. Preferably, the transition from the "known state" to the "ambient state" is permitted without additional heating and/or cooling being applied to the humidity sensor.

Figure 5:
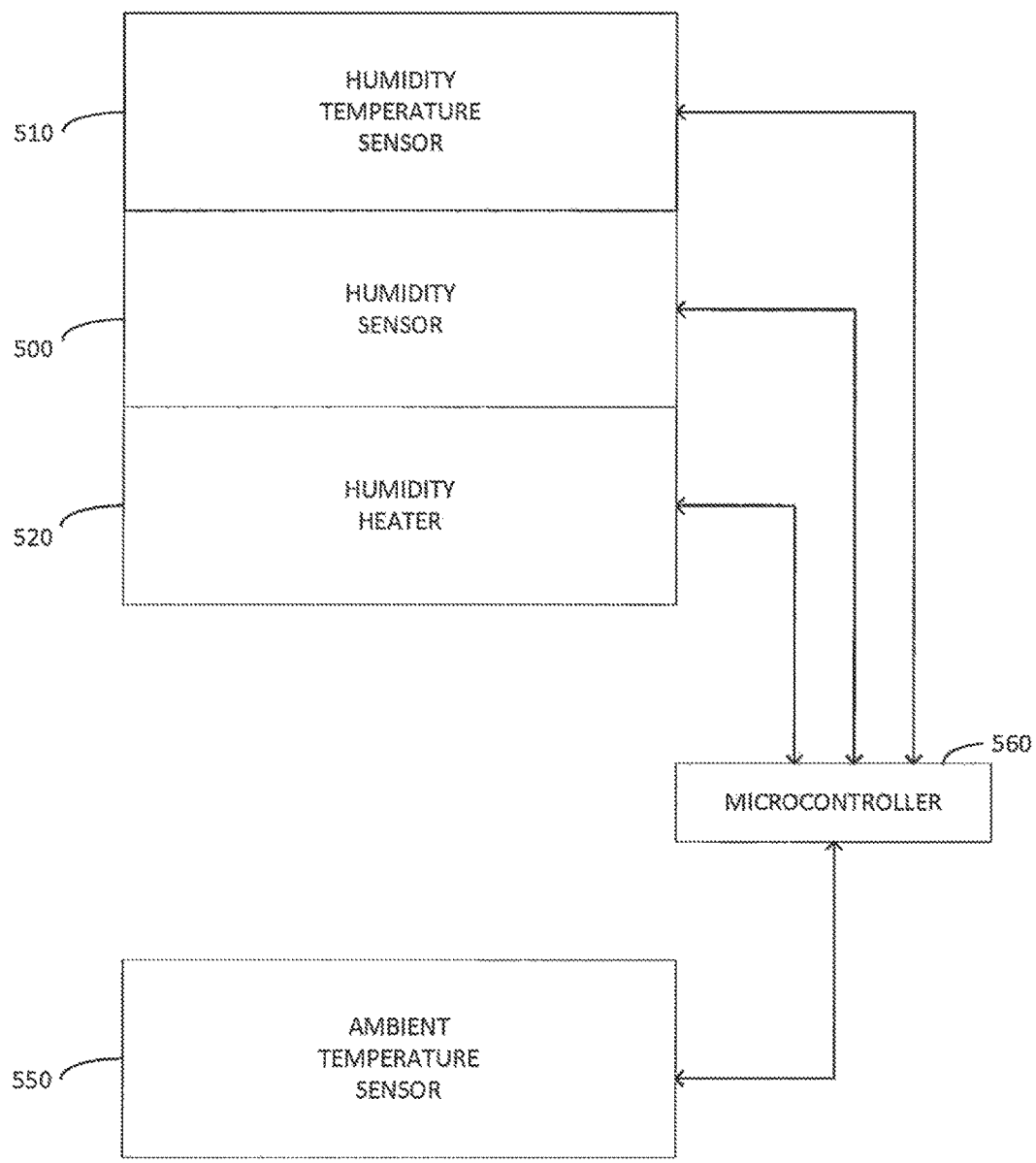
FIG. 5 illustrates an exemplary humidity sensing system.

Referring to FIG. 5, a humidity sensing system may include a humidity sensor 500. Associated with the humidity sensor 500 may be a humidity temperature sensor 510 that senses the temperature of the humidity sensor 500. In addition, associated with the humidity sensor 500 may be a humidity heater 520 that selectively increases the temperature of the humidity sensor 500. Also, associated with the humidity sensing system may include an ambient temperature sensor 550 that senses the ambient temperature of the humidity sensor's 500 environment. A microcontroller 560 may provide signals to and receive signals from the different components of the humidity sensing system. In addition, the humidity sensing system may include additional components, not illustrated, to effectuate suitable measurements.

Figure 6:
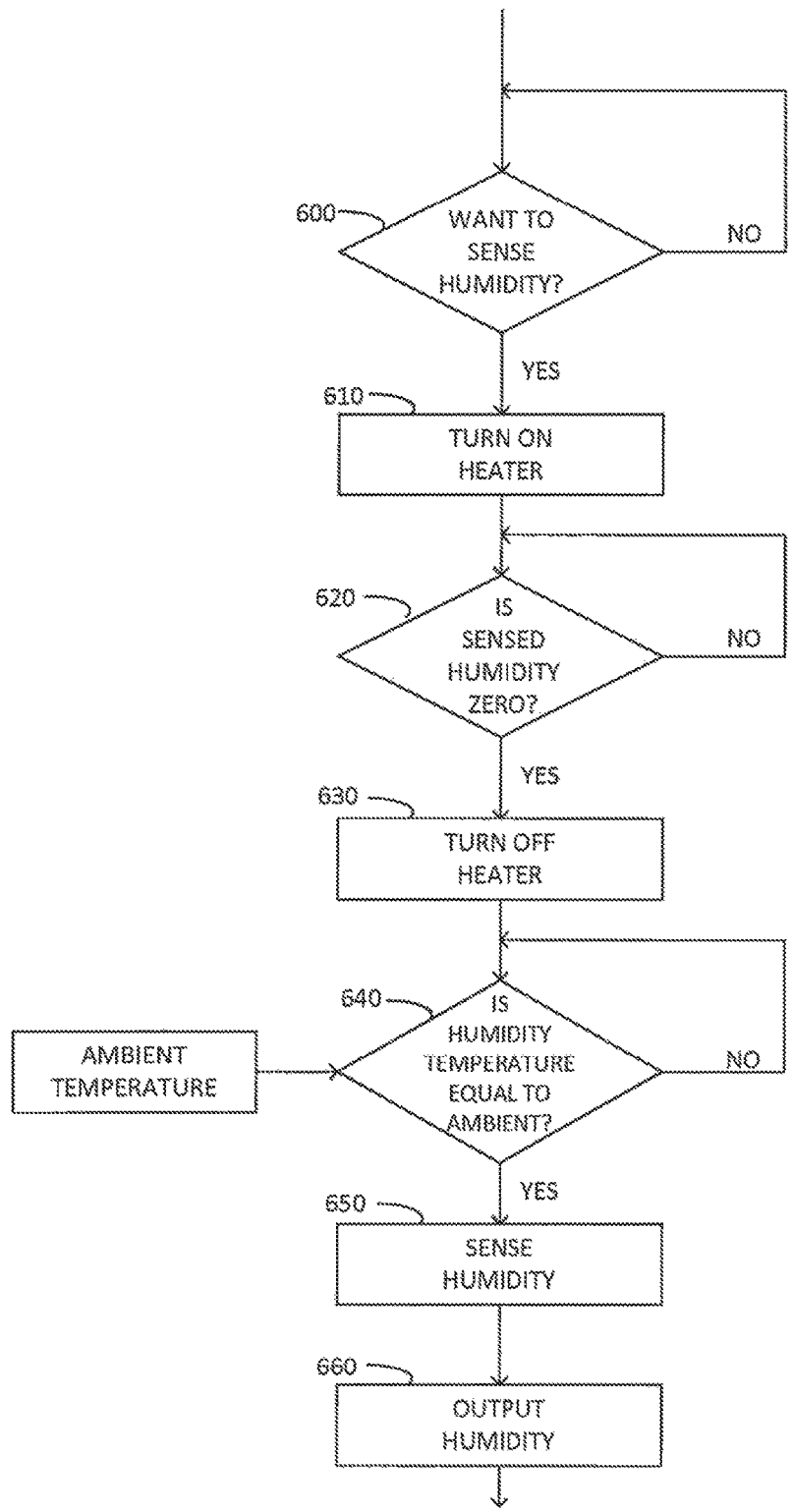
FIG. 6 illustrates an exemplary humidity sensing process.

Referring to FIG. 6, a determination is made that it is desirable to sense humidity 600. When it is desired to measure the humidity, it is desirable to decrease the humidity sensed by the humidity sensor 500. The humidity heater 520 proximate the humidity sensor is turned on 610 (or otherwise increased) to decrease the humidity sensed by the humidity sensor 500. The humidity sensed by the humidity sensor 500 is periodically sensed 620 until the sensed humidity is sufficiently low, such as zero. At this point, the humidity sensor 500 is at a generally known state with no substantial hysteresis. The humidity heater 520 is turned off 630 (or otherwise reduced). The microcontroller 560 compares the humidity temperature from the humidity temperature sensor 510 to the ambient temperature from the ambient temperature sensor 550 until they are sufficiently similar 640. Then the temperature of the humidity sensor 500 is sufficiently close to the ambient temperature, indicating that the humidity sensor 500 has absorbed moisture representative of the existing humidity in the environment of the humidity sensor 500, the humidity is sensed 650 by the humidity sensor 500. The microcontroller 560 may output 660 the sensed humidity in any suitable manner, such as a display, a 4-20 ma signal, a digital signal, or otherwise setting a set of registers of the humidity sensing system that may be queried.

This process of resetting the state of the sensor preferably occurs between each subsequent measurement. Accordingly, the rate at which the sensing of humidity by the humidity sensor may be somewhat limited, but the accuracy of each of the measurements is substantially increased.

Figure 7:
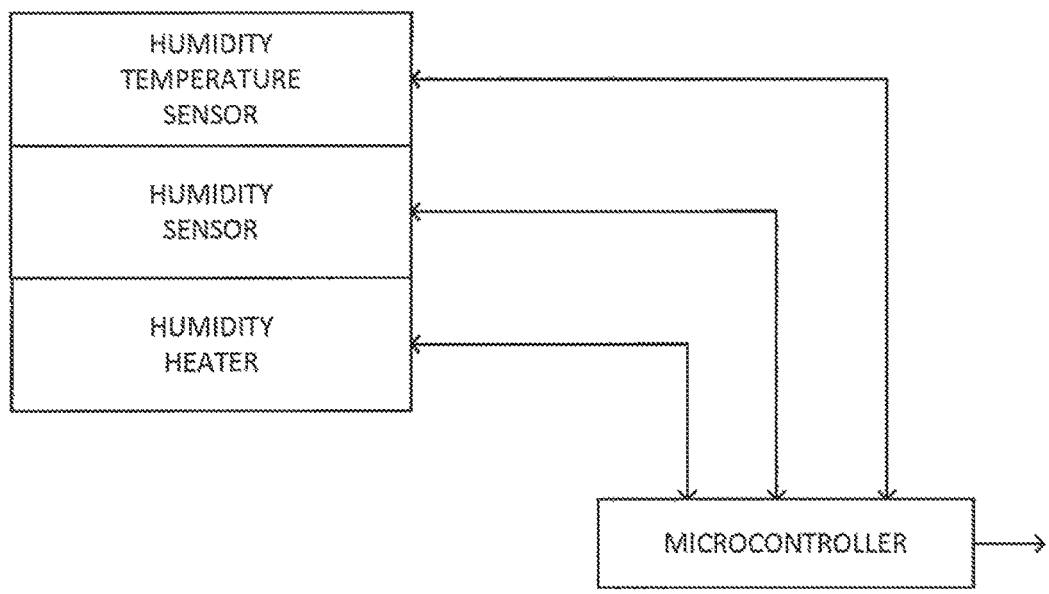
FIG. 7 illustrates another exemplary humidity sensing system.

Referring to FIG. 7, another embodiment may include a humidity sensor system that includes a humidity sensor, a humidity heater, and a humidity temperature sensor. In this embodiment, the system does not include the ambient reference temperature sensor to determine when to obtain the humidity measurement. As a result, the microcontroller after sufficiently removing the humidity from the humidity sensor using the humidity heater, the system may measure a series of humidity measurements and based upon the characteristics of the resulting measurements, may determine the ambient humidity.

Figure 8:
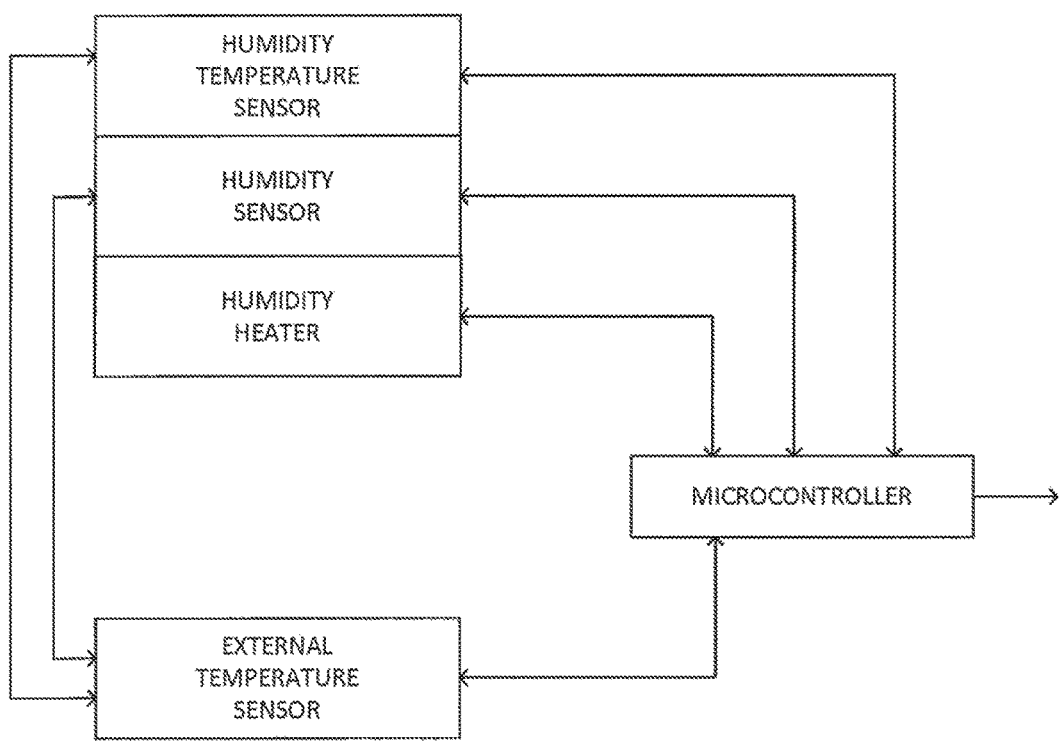
FIG. 8 illustrates another exemplary humidity sensing system.

Referring to FIG. 8, another embodiment may include a humidity sensor system that includes a humidity sensor, a humidity heater, a humidity temperature sensor, together with an external ambient temperature sensor. In this embodiment, the external ambient temperature sensor may synchronize the temperature with the humidity temperature sensor and control the humidity sensor sampling. As a result, the microcontroller after sufficiently removing the humidity from the humidity sensor using the humidity heater, the system may determine the humidity by being provided with the measurement at the appropriate time.

Figure 9:
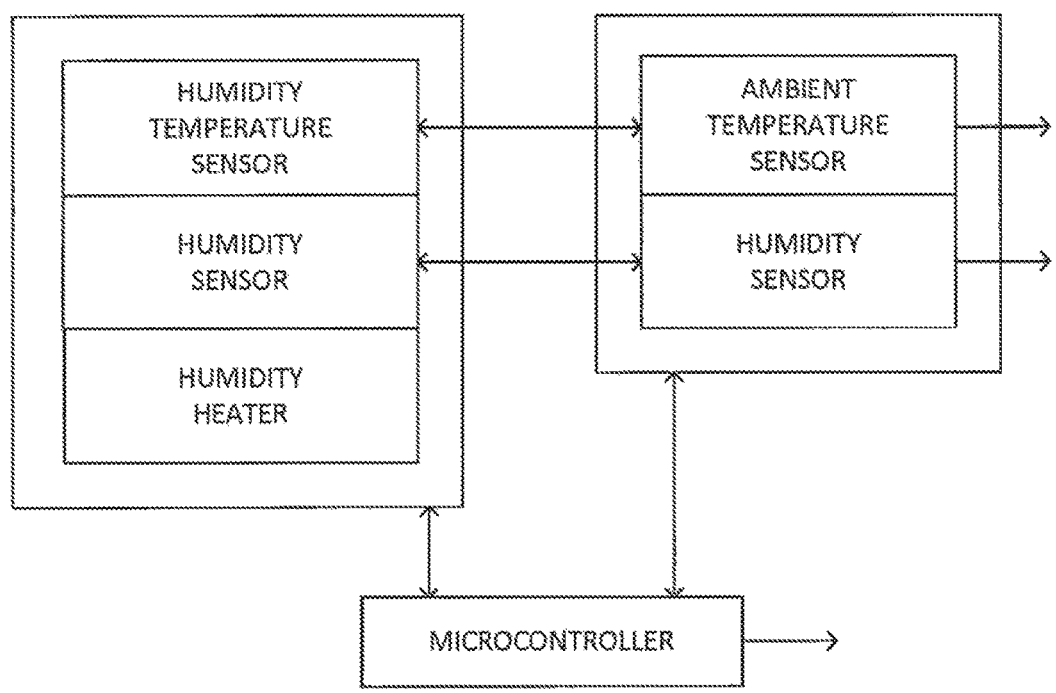
FIG. 9 illustrates another exemplary humidity sensing system.

Referring to FIG. 9, another embodiment may include a humidity sensor system that includes a humidity sensor, a humidity heater, a humidity temperature sensor, together with an external ambient temperature sensor combined with an external humidity sensor. In this embodiment, the external ambient temperature sensor may synchronize the temperature with the humidity temperature sensor and control the humidity sensor sampling, if desired. In this embodiment, the external humidity sensor may synchronize the humidity measurements of the two humidity sensors. As a result, the microcontroller after sufficiently removing the humidity from the humidity sensor using the humidity heater, the system may determine the humidity by being provided with the measurement at the appropriate time.

It is to be understood that the microcontroller may be omitted, if desired. It is to be understood that the microcontroller may be integrated with the humidity sensor, if desired.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:
1. A method for sensing humidity comprising providing a humidity sensing system and further comprising:
  (a) providing a humidity sensitive material;
  (b) providing a sensing circuit associated with said humidity sensitive material causing the sensing circuit to estimate the humidity based upon said humidity sensitive material;
  (c) providing a heating element associated with said humidity sensitive material;
  (d) providing a first temperature sensor associated with said humidity sensing system capable of sensing the temperature proximate said humidity sensitive material and providing a second temperature sensor associated with said humidity sensing system capable of sensing an ambient temperature an environment relative to said humidity sensitive material;
  (e) providing a temperature circuit, causing the temperature circuit to temporarily increase the temperature proximate said humidity sensitive material, causing the sensing circuit to take a first estimate of the humidity based upon said humidity sensor, causing the temperature circuit to maintain the increased temperature proximate said humidity sensitive material if the first estimate of the humidity is not sufficiently low, causing the sensing circuit to take a second estimate of the humidity based upon said humidity sensor, causing the temperature circuit to discontinue the increased temperature proximate said humidity sensitive material and thereafter causing said sensing circuit to estimate said humidity when temperature proximate said humidity sensitive material is sufficiently close to an ambient temperature based upon said sensing by said first temperature sensor proximate said humidity sensitive material and said second temperature sensor in said environment relative to said humidity sensitive material.

2. The method of claim 1 wherein said humidity sensor is a capacitance based sensor.

3. The method of claim 2 wherein said humidity sensor has a dielectric film core.

4. The method of claim 3 wherein said film core has a pair of electrically conductive layers on opposite sides thereof.

5. The method of claim 1 wherein said humidity sensitive material has backbone chains containing heterocyclic units.

6. The method of claim 5 wherein said heterocyclic unit has an oxygen atom double bonded.

7. The method of claim 5 wherein said heterocylic units include at least one keto group.

8. The method of claim 1 wherein said humidity sensitive material is less than 0.005 inches thick.

9. The method of claim 1 wherein said temperature increase is sufficient to reduce a sensed humidity based upon said humidity sensitive material to be less than 10% of a full scale measurement.

10. The method of claim 1 wherein said temperature increase is sufficient to reduce a sensed humidity based upon said humidity sensitive material to be less than 5% of a full scale measurement.

11. The method of claim 1 wherein said temperature increase is sufficient to reduce a sensed humidity based upon said humidity sensitive material to be less than 3% of a full scale measurement.

12. The method of claim 1 wherein said temperature increase is sufficient to reduce a sensed humidity based upon said humidity sensitive material to be less than 1% of a full scale measurement.

13. The method of claim 1 wherein said temperature increase is sufficient to reduce a sensed humidity based upon said humidity sensitive material to be 0% of a full scale measurement.

14. The method of claim 1 wherein said sufficiently close is said temperature proximate said humidity sensitive material is less than 10% difference to said ambient temperature proximate said humidity sensitive material.

15. The method of claim 1 wherein said sufficiently close is said temperature proximate said humidity sensitive material is less than 5% difference to said ambient temperature proximate said humidity sensitive material.

16. The method of claim 1 wherein said sufficiently close is said temperature proximate said humidity sensitive material is less than 3% difference to said ambient temperature proximate said humidity sensitive material.

17. The method of claim 1 wherein said sufficiently close is said temperature proximate said humidity sensitive material is less than 1% difference to said ambient temperature proximate said humidity sensitive material.

18. The method of claim 1 wherein said sufficiently close is said temperature proximate said humidity sensitive material is the same as said ambient temperature proximate said humidity sensitive material.

* * * * *